United States Patent [19]
Covarrubias

[11] Patent Number: 5,472,002
[45] Date of Patent: Dec. 5, 1995

[54] CIGARETTE FILTER FOR ADMINISTERING TAURINE BY INHALATION

[76] Inventor: Jesus Covarrubias, 2° Cerrada de San Jeronimo 110, Mexico 20 - DF, Mexico

[21] Appl. No.: 128,711

[22] Filed: Sep. 30, 1993

[30] Foreign Application Priority Data

Sep. 30, 1992 [FR] France .................................. 92 11645

[51] Int. Cl.$^6$ ........................................... A24D 1/04
[52] U.S. Cl. .......................................... 131/335; 131/337
[58] Field of Search ................................. 131/331–337

[56] References Cited

U.S. PATENT DOCUMENTS

| | | | |
|---|---|---|---|
| 1,826,331 | 10/1931 | Traube | 131/173 |
| 2,547,119 | 4/1951 | Henderson | 131/349 |
| 2,863,461 | 12/1958 | Frost | 131/337 |
| 3,635,226 | 1/1972 | Horsewell et al. | |
| 3,991,773 | 11/1976 | Walker | |
| 4,498,485 | 2/1985 | Carter | |

FOREIGN PATENT DOCUMENTS

| | | | |
|---|---|---|---|
| 0307788 | 3/1989 | European Pat. Off. | |
| 1270933 | 7/1961 | France | 131/337 |
| 1204018 | 9/1970 | United Kingdom | 131/337 |

OTHER PUBLICATIONS

Gordon et al., "Taurine Protects Hamster Bronchioles From Acute $NO_2$–Induced Alterations", AJP pp. 585–560, Dec. 1986.

G. E. Gaull, "Taurine as a Conditionally Essential Nutrient in Man", J. of Am. College of Nutrition 5:121–125 (1986), pp. 121–125.

Laidlaw et al, "Antimutagenic Effects of Taurine–A Baceterial Assay System", Cancer Research 49, 6600–6604 (Dec. 1989).

Ferreira et al, "Reduction of Reperfusion Injury During Myocardial Revascularization with Taurine Bolus", University of Milan, 15–20 Jul. 1990, pp. 35–38.

Kimura et al, "Treatment of Smoke–Induced Pulmonary Injury by Nebulized Dimethylsulfoxide", Alan R. Riss, Inc. (1988), pp. 333–341.

*Primary Examiner*—Jennifer Bahr
*Attorney, Agent, or Firm*—Oblon, Spivak, McClelland, Maier, & Neustadt

[57] ABSTRACT

The invention relates to a device for administering taurine to smokers by inhalation.

The device consists of a cigarette filter which comprises:
- a filtration material for filtering the smoke from burning tobacco which passes through said filtration material, and
- means for including taurine into said filtration material and introducing it into the smoke as it passes through said filtration material.

The device is useful for the prevention of diseases of respiratory ducts of smokers.

10 Claims, 1 Drawing Sheet

CIGARETTE FILTER FOR ADMINISTERING TAURINE BY INHALATION

FIELD OF THE INVENTION

The present invention relates to a device for oral delivery of medicinal or nutritional substances, and more particularly to a device for administering a pharmacologically active substance such as taurine to the lungs of a smoker, by inhalation, especially in a prevention treatment of the diseases of the respiratory ducts.

DISCUSSION OF THE BACKGROUND

Several devices are known where active or aromatic substances are introduced in a cigarette in order to modify its taste or to confer additional properties. For example, U.S. Pat. No. 3,991,773 and U.S. Pat. No. 3,635,226 describe mechanisms for humidifying cigarette smoke by including rupturable capsules or micro-capsules filled with a liquid, within the filter of the cigarette. The smoker may obtain the humidification by squeezing the filter to rupture the capsules, or may leave the capsules unruptured to inhale dry smoke. The liquid incorporated in the capsules may contain flavourings or a synthetic saliva solution, for example.

It is also known to include a substance exhibiting medicinal properties in the tobacco of the cigarette. U.S. Pat. No. 4,498,485 discloses the inclusion of interferon into the tobacco of a cigarette for administering it directly to the lungs of the smoker.

Taurine (or 2-aminoethane sulfonic acid) is an amino acid having a low toxicity, possessing some known pharmacological properties which may be useful in therapy for the treatment of congestive heart failure, but the activity of taurine is very low and it cannot be efficiently used as a drug. Taurine amides showing mucolytic, hepatoprotective, detoxicant and normolipemizing properties are described in European patent application 307,788.

SUMMARY OF THE INVENTION

R. E. Gordon et al., in an article entitled "Taurine Protects Hamster Bronchioles From Acute $NO_2$-Induced Alterations", *AJP* (Dec. 1986), describe the use of taurine in the feeding of hamsters, which results in an improvement of the protection against the adverse effects of nitrogen dioxide $NO_2$ which is a, component of urban pollution and is included in the tobacco smoke. According to an hypothesis disclosed in said article, taurine is distributed through the tissues of the animal and participates in a variety of biochemical reactions to stabilize membranes, scavenge free radicals and prevent from peroxidation. The protective effect of taurine on membranes and against toxic compounds such as oxidants, is also described in G.E. Gaull "Taurine as a Conditionally Essential Nutrient in Man", *J. of Am. College of Nutrition* 5:121–125 (1986), which considers such effects in human subjects.

More recently, the intravenous administration of taurine in patients who have undergone coronary artery bypass surgery, was shown to reduce myocardial damages by producing an antioxidant and scavenging effect. Reference can be made to Ferreira et al. "Reduction of Reperfusion Injury During Myocardial Revascularization with Taurine Bolus" University of Milan, Jul. 15–20, 1990.

It has also been demonstrated that the administration of dimethylsulfoxide, in nebulized form, by inhalation, is effective in the treatment of smoke-induced pulmonary injury. Reference can be made to Kimura et al. in "Treatment of Smoke-Induced Pulmonary Injury by Nebulized Dimethylsulfoxide", Alan R. Riss, Inc. (1988). These results are based on animal experiments.

Other published experimentation results have established the usefulness of taurine in producing anti-mutagenic effects by inhibiting various supposed carcinogenic agents which may induce changes in DNA. These agents contain reactive free radicals. Reference can be made to Laidlaw et al. in "Anti-Mutagenic Effects of Taurine—A Bacterial Assay System", *Cancer Research*, 49, 6600–6604 (Dec. 1989).

An object of the present invention is a device for administering taurine to smokers, by inhalation.

More particularly, an object of the invention is to provide a cigarette filter comprising a filtration material for filtering smoke from burning tobacco which passes through said filtration material, and means for including taurine into said filtration material and introducing it into the smoke as it passes through said filtration material.

A further object of the present invention is to provide a method for administering taurine to the lungs of a smoker, which comprises introducing taurine into the filter of a cigarette, in the form of a powder or a solution of taurine.

According to a preferred embodiment, the device according to the present invention comprises:
- a filtration material for filtering smoke from burning tobacco as it passes through said filtration material;
- at least one rupturable capsule containing water or an aqueous solution, located in said filtration material, so that the capsule is ruptured by a pressure on the filter and the water or the aqueous solution is distributed into the filtration material.

Taurine can be in the form of a powder included in the filtration material which further contains at least one capsule containing water or an aqueous solution, or in the form of a solution contained in the capsule(s) included in the filtration material. When taurine is in the form of powder, it is preferably associated with microcapsules containing water, distributed in the filtration material.

BRIEF DESCRIPTION OF THE DRAWINGS

The characteristics of the present invention will be described in detail in the following description, relating to a preferred embodiment, with reference to the annexed drawings, which represent.

DESCRIPTION OF THE PREFERRED EMBODIMENTS

Figure 1:
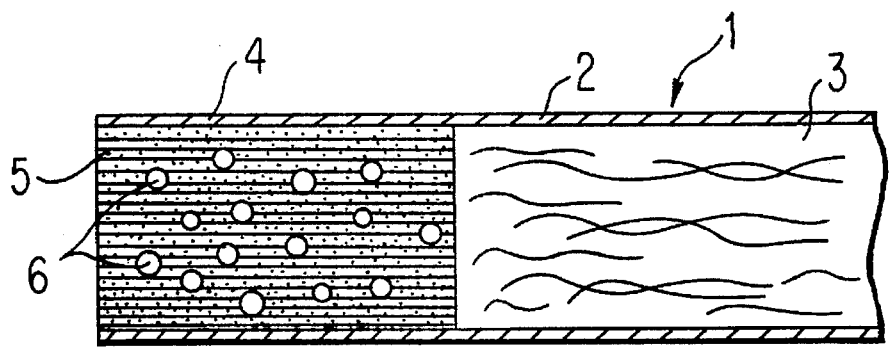
FIG. 1: a longitudinal sectional view of the filter end of a cigarette comprising the device according to the invention.

As represented on FIG. 1, the device according to the invention comprises a filter end (1) of a cigarette comprising a paper (2) forming a wrapping material containing tobacco (3) and a filter consisting of a filtration material (4), such as packed cellulose or similar fibers.

According to the present invention, means for introducing taurine into the filtration material are provided in the form of finely divided taurine powder (5), which is uniformly distributed through the filtration material (4). The powder, which should be the consistency of light talcum powder, is automatically drawn into the smoke as it passes from the burning tobacco (3) through the filtration material (4) to the smoker's lungs.

If necessary, according to the invention, a solution of taurine can be distributed through the filtration material (4) by rolling the filter (1) between the fingers to crush and rupture the walls of the microspheres (6) containing distilled water, a physiological saline or a non toxic aqueous solution. Thus, crushing the microspheres by exerting a slight pressure onto the filter and rolling it between the fingers, results in the rupture of the thin walls, for example made of epoxy resin or any other inert substance, and the aqueous solution or water contained therein is thus distributed through the filtration material (4) and forms a solution with the taurine powder, since taurine is water soluble.

The presence of a taurine solution in the filtration material which is passed by rapidly moving smoke, which is warm, facilitates some evaporation and some atomisation of the solution which is then carried into the smoker's lungs.

Figure 2:
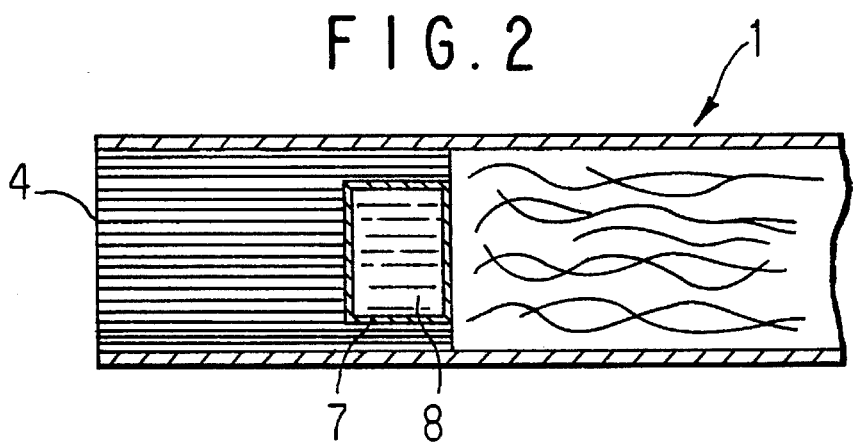
FIG. 2: a sectional view of a filter representing a second embodiment of the invention.
Figure 3:
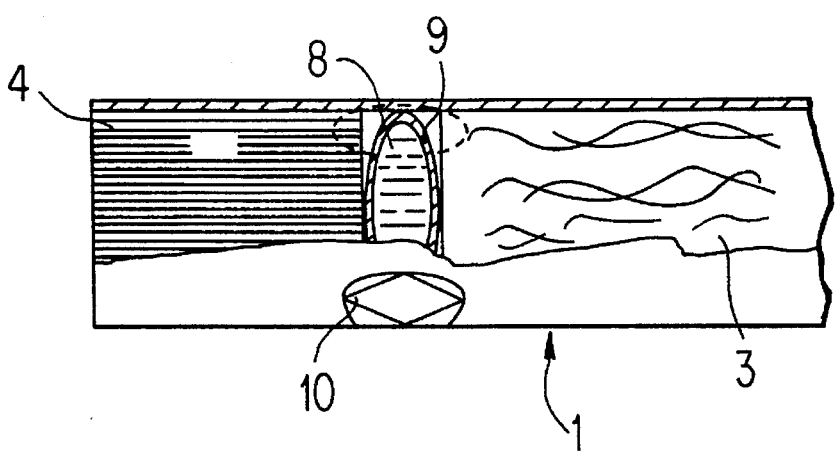
FIG. 3: a sectional view of a filter representing a third embodiment of the invention.

FIGS. 2 and 3 represent two other embodiments of the present invention, where the same references are used to designate the same parts as in FIG. 1.

FIG. 2 represents a rupturable capsule (7) having a waterproof wall, containing a taurine solution (8), positioned in the middle of the filtration material (4) near the junction with the tobacco. By pressing the filter near said junction, the capsule is crushed, the walls are ruptured, and the taurine solution is distributed through the filtration material.

FIG. 3 represents a third embodiment of the filter according to the present invention wherein an oblong shaped capsule (9) is located in the space, within the paper (2), between the tobacco (3) and the filtration material (4). Markings or references (10) are provided on the outer surface of the paper (2) so that the smoker can locate the area where to squeeze the cigarette for crushing the capsule (9) and rupturing the walls thereof. Although the major part of the taurine solution (8) seeps into the filtration material (4) and into the joining tobacco (3), a small part of the solution remains in the space between the tobacco (3) and the filtration material (4) where it is used as means for humidifying and introducing taurine solution into the smoke passing through the filter.

The embodiments represented in FIGS. 2 and 3 may also be modified by providing distilled water or other aqueous solution into the capsules (7) and (9), the taurine powder being positioned in the filtration material (4). According to the invention, the filter can be as represented in FIG. 1, and it does not contain the rupturable spheres but it only contains powdered taurine.

A particular advantage resulting from the presence of taurine in the filter, either in the form of powder or in the form of a solution, is that the decomposition temperature of taurine is 300° C. Introducing taurine into the tobacco charge would thus substantially annihilate the desired purpose of the invention since taurine would be decomposed as the burning tobacco progressed toward the filter. Thus, the invention differs from U.S. Pat. No. 4,498,485, which describes the inclusion of a pharmacologically active substance, such as interferon, in the tobacco of a cigarette.

The presence of even small amounts of taurine in the smoke of a cigarette provides an efficient taurine delivery system.

When it is administered to the lungs, taurine has an advantageous anti-oxidant effect, which is known as indicated above. This effect is potentiated when the administration of taurine takes place in the presence of the smoke of a burning cigarette exhibiting an anti-oxidant effect. Although the activity of taurine is supposed to be effective mainly in the lungs, it may also act directly on the smoke by a "buffer" effect, before the smoke reaches the smoker's lungs.

Further, the administration of taurine by inhalation, by using the device according to the present invention, substantially differs from the administration by oral route, namely as nutritional additive, and it does not result in the same effects. When taurine is administered orally as usual, it is exposed to the acid medium of the stomach and it is absorbed in the gastrointestinal tract. In contrast, according to the invention, taurine is directly contacted with the internal wall of the lungs. As indicated above, the effect of taurine is potentiated, even with relatively small quantities of taurine introduced in the cigarette filter.

It has been noted that the administration of taurine by using the device according to the invention provides a protective effect against the harmful effects of the smoke resulting from the burning tobacco, verified by the test of bronchospasms induced by ultrasonic nebulization of distilled water. A decrease in the bronchospasms is observed when taurine is regularly administered by using the device according to the invention.

The taurine solution contained in the capsules of the device represented in FIGS. 2 and 3, is preferably a solution having a taurine content from 0.2% to 2.0% by weight. The water containing microspheres of the device represented in FIG. 1 must be introduced in the filtration material in such a quantity that the concentration of the resulting taurine solution is of about 100 mg/ml. The total amount of taurine present in the filter is generally comprised between 25 mg and 200 mg, and preferably between 50 mg and 120 mg.

I claim:

1. A device for administering taurine by inhalation, comprising a cigarette filter having an inlet end and an outlet end, said cigarette filter comprising:

a filtration material disposed between said inlet end and said outlet end for filtering the smoke from burning tobacco which enters said inlet end, passes through said filtration material and exits said outlet end, taurine, and means for including taurine into said filtration material and introducing it into the smoke as it passes through said filtration material.

2. The device according to claim 1, which comprises:

a filtration material for filtering smoke;

at least one rupturable capsule containing water or an aqueous solution, located in said filtration material, so that the capsule is ruptured by a pressure on the filter, and the water or the aqueous solution is distributed into the filtration material.

3. The device according to any of claims 1 and 2, wherein said filtration material contains rupturable microspheres containing water or an aqueous solution.

4. The device according to any of claims 1 and 2, wherein taurine is in the form of a powder introduced into the filtration material.

5. The device according to any of claims 1 and 2, wherein taurine is in the form of a solution contained in at least one rupturable capsule introduced into the filtration material.

6. The device according to claim 2, further including a paper surrounding said at least one rupturable capsule and including a marking on said paper to identify a location to squeeze and rupture said at least one rupturable capsule.

7. The device of claim 1, wherein said taurine is present in the amount of 25 mg to 200 mg.

8. The device of claim 5, wherein said solution has a taurine content of from 0.2% to 2.0% by weight.

9. The device of claim 1, further including a supply of tobacco.

10. The device of claim 2, further including a supply of tobacco.

* * * * *